(12) United States Patent
Madsen

(10) Patent No.: US 7,191,782 B2
(45) Date of Patent: Mar. 20, 2007

(54) RESPIRATORY SUCTION CATHETER APPARATUS CONFIGURED FOR RELEASABLE ATTACHMENT WITH AN ARTIFICIAL AIRWAY STRUCTURE

(75) Inventor: Edward B. Madsen, Riverton, UT (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 455 days.

(21) Appl. No.: 10/430,812

(22) Filed: May 6, 2003

(65) Prior Publication Data

US 2004/0221851 A1  Nov. 11, 2004

(51) Int. Cl.
*A61M 16/00* (2006.01)
(52) U.S. Cl. ............................ 128/207.14; 128/200.26; 128/207.16
(58) Field of Classification Search ........... 128/207.14, 128/207.16, 200.26, 912, 207.15, 201.26; 604/96.01, 35, 43, 73, 93.01, 264, 268, 523, 604/537, 402, 541, 542, 543
See application file for complete search history.

(56) References Cited

U.S. PATENT DOCUMENTS

| | | | |
|---|---|---|---|
| 3,991,762 A | 11/1976 | Radford |
| 4,152,017 A | 5/1979 | Abramson |
| 4,416,273 A | 11/1983 | Grimes |
| 4,510,933 A | 4/1985 | Wendt et al. |
| 4,569,344 A | 2/1986 | Palmer |
| 4,573,965 A | 3/1986 | Russo |
| 4,607,635 A | 8/1986 | Heyden |
| 4,638,539 A | 1/1987 | Palmer |
| 4,696,296 A | 9/1987 | Palmer |
| 4,762,125 A | 8/1988 | Leiman et al. |

(Continued)

FOREIGN PATENT DOCUMENTS

EP   1210957   6/2002

(Continued)

OTHER PUBLICATIONS

U.S. Patent Application BAL-120 (18273), Edward B. Madsen, et al., Filed May 6, 2003.

(Continued)

*Primary Examiner*—Teena Mitchell
*Assistant Examiner*—Amadeus Lopez
(74) *Attorney, Agent, or Firm*—Dority & Manning

(57) ABSTRACT

A respiratory suction catheter apparatus includes a suction catheter that has a tubular portion with a distal end. The suction catheter may be adapted for removing fluids from a patient by insertion of the tubular portion into an artificial airway of the patient and application of negative pressure to a lumen of the tubular portion. A catheter attachment section is present and has a proximal end that is attached to the suction catheter, and has a distal end that is configured for releasable attachment with an artificial airway structure that is attached to the patient. A valve is located in the catheter attachment section. The valve has a closed position that at least substantially blocks the passageway of the catheter attachment section which causes the tubular portion to be substantially isolated from the artificial airway of the patient. The valve has an open position that allows the tubular portion of the suction catheter to be advanced through the catheter attachment section and into the artificial airway of the patient.

27 Claims, 14 Drawing Sheets

U.S. PATENT DOCUMENTS

| | | |
|---|---|---|
| 4,836,199 A | 6/1989 | Palmer |
| 4,846,167 A | 7/1989 | Tibbals |
| 4,872,579 A | 10/1989 | Palmer |
| 5,062,420 A | 11/1991 | Levine |
| 5,083,561 A | 1/1992 | Russo |
| 5,139,018 A | 8/1992 | Brodsky et al. |
| 5,199,427 A | 4/1993 | Strickland |
| 5,218,957 A | 6/1993 | Strickland |
| 5,220,916 A * | 6/1993 | Russo ................... 128/207.16 |
| 5,230,332 A | 7/1993 | Strickland |
| 5,254,098 A | 10/1993 | Ulrich et al. |
| 5,255,676 A | 10/1993 | Russo |
| 5,349,950 A | 9/1994 | Ulrich et al. |
| 5,355,876 A | 10/1994 | Brodsky et al. |
| 5,433,195 A | 7/1995 | Kee et al. |
| 5,445,141 A | 8/1995 | Kee et al. |
| 5,513,628 A | 5/1996 | Coles et al. |
| 5,582,161 A | 12/1996 | Kee |
| 5,582,165 A | 12/1996 | Bryan et al. |
| 5,598,840 A | 2/1997 | Iund et al. |
| 5,645,048 A | 7/1997 | Brodsky et al. |
| 5,664,564 A | 9/1997 | Palmer |
| 5,664,594 A | 9/1997 | Kee |
| 5,676,136 A | 10/1997 | Russo |
| 5,694,922 A | 12/1997 | Palmer |
| 5,711,294 A | 1/1998 | Kee et al. |
| 5,730,123 A | 3/1998 | Lorenzen et al. |
| 5,735,271 A * | 4/1998 | Lorenzen et al. ...... 128/207.16 |
| 5,738,091 A | 4/1998 | Kee et al. |
| 5,775,325 A | 7/1998 | Russo |
| 5,779,687 A | 7/1998 | Bell et al. |
| 5,791,337 A * | 8/1998 | Coles et al. ........... 128/200.26 |
| 5,882,348 A * | 3/1999 | Winterton et al. .......... 604/537 |
| 6,012,451 A | 1/2000 | Palmer |
| 6,026,810 A | 2/2000 | Baird |
| 6,082,361 A | 7/2000 | Morejon |
| 6,165,168 A | 12/2000 | Russo |
| 6,227,200 B1 * | 5/2001 | Crump et al. ........... 128/207.16 |
| 6,318,368 B1 | 11/2001 | Morejon |
| 6,494,203 B1 | 12/2002 | Palmer |
| 6,543,451 B1 * | 4/2003 | Crump et al. ........... 128/207.14 |
| 6,584,970 B1 * | 7/2003 | Crump et al. ........... 128/200.24 |
| 6,588,425 B2 * | 7/2003 | Rouns et al. ........... 128/207.14 |
| 6,602,219 B2 * | 8/2003 | Madsen et al. ................ 604/27 |
| 6,612,304 B1 * | 9/2003 | Cise et al. ............. 128/200.26 |
| 6,615,835 B1 * | 9/2003 | Cise et al. ............. 128/207.14 |
| 2002/0078960 A1 | 6/2002 | Cise |

FOREIGN PATENT DOCUMENTS

| | | |
|---|---|---|
| GB | 2199630 A | 7/1988 |
| WO | WO 9531250 | 11/1995 |
| WO | WO 9609082 | 3/1996 |
| WO | WO 9626757 | 9/1996 |
| WO | WO 0015284 | 3/2000 |
| WO | WO 0024439 | 5/2000 |
| WO | WO 0141853 A1 | 6/2001 |
| WO | WO 0141855 A1 | 6/2001 |
| WO | WO 0145779 A1 | 6/2001 |
| WO | WO 0228463 A2 | 4/2002 |
| WO | WO 0249680 A2 | 6/2002 |
| WO | WO 0249699 A2 | 6/2002 |
| WO | WO 02055143 A2 | 7/2002 |

OTHER PUBLICATIONS

U.S. Patent Application BAL-119 (18267), Edward B. Madsen, Filed May 6, 2003.
International Search Report PCT/US2004/002626.
PCT Written Opinion of the International Searching Authority of PCT/US2004/002626.

* cited by examiner

RESPIRATORY SUCTION CATHETER APPARATUS CONFIGURED FOR RELEASABLE ATTACHMENT WITH AN ARTIFICIAL AIRWAY STRUCTURE

BACKGROUND

A variety of different circumstances exist in which a person may be required to have a catheter inserted into their body for a medical procedure. Once such use for a catheter exists when a person needs to have an artificial airway, such as an endotracheal tube, placed in his or her respiratory system. During surgery, for instance, the artificial airway's primary function is to keep the patient's airway open so that adequate lung ventilation can be maintained during the surgical procedure. Alternatively, with many patients the endotracheal tube will remain in place to sustain mechanical ventilation for a prolonged period.

If an endotracheal tube is to be left in place for any substantial amount of time, it is critical that respiratory secretions be periodically removed. This is usually accomplished with the use of a respiratory suction catheter. As the suction catheter is withdrawn, a negative pressure may be applied to the interior of the catheter to draw mucus and other secretions from the respiratory system.

With conventional closed suction catheter assemblies, for example as the one set forth in U.S. Pat. No. 4,569,344 issued to Palmer, which is incorporated by reference herein in its entirety for all purposes, the catheter tube is enveloped by a protective sleeve. The catheter assembly includes a valve mechanism in communication with a vacuum source to control the suctioning process. At its distal or patient end, the closed suction catheter assembly is permanently attached to a manifold, connector, adaptor, or the like.

After the application of negative pressure, the catheter tube may be withdrawn from the artificial airway and, as the catheter tube is pulled back into the protective sleeve, a wiper or seal strips or scrapes a substantial portion of any mucus or secretions from the outside of the catheter tube. However, the distal tip portion of the catheter tube may not pass through the seal or wiper and thus any secretions or mucus on the distal end must be removed by other means. It is desirable to remove these secretions from the catheter tube in order to prevent contamination from infectious agents that may be present in the respiratory secretions. Patients using artificial airways often have compromised immune systems and are more susceptible to infectious agents.

Several mechanisms exist by which a catheter may be cleaned. For example, a lavage port may be included which enables the clinician to inject liquid into the area surrounding the tip of the catheter after it has been withdrawn from the patient's airway. When liquid is injected and suction is applied, the liquid helps to loosen and remove the secretions from the exterior of the catheter.

One significant problem with simply injecting liquid and applying suction is that the suction also causes a volume of respiratory air to be removed through the catheter. In a closed system, the air that is evacuated potentially disrupts the carefully controlled ventilation cycle and the amount of respiratory air available to the patient may be decreased as a result of catheter cleaning.

Prior respiratory suction catheter apparatuses have been developed in order to allow for cleaning of the distal tip of the catheter without substantially interrupting the airflow to the patient from the ventilator. U.S. Pat. No. 6,227,200 B1 issued to Crump et al., which is incorporated by reference herein in its entirety for all purposes, provides in one exemplary embodiment a flap valve that may be used to substantially isolate the distal end of the catheter from the patient's airway during cleaning. The flap valve also has an open position in which the catheter may be inserted through the manifold into the airway of the patient. Prior respiratory suction catheter apparatuses incorporate the flap valve and related structure such that these parts are permanently bonded to the manifold.

Although respiratory suction catheter apparatuses are provided with a cleaning mechanism in order to remove mucus and other infectious agents, it is often the case that the catheter itself needs to be regularly replaced in order to insure a more sterile respiratory circuit. Some manufacturers recommend replacement of the suction catheter every 24 hours with a new suction catheter. In the instance when the suction catheter needs to be replaced, the artificial airway structure, often a manifold, into which the flap valve and related parts are contained, and onto which the suction catheter is attached, is detached from the respiratory circuit. This detachment necessarily interferes with the supply of air to the patient, and increases the chance of ventilator associated complications. The new manifold having the catheter and valve is then attached to the ventilator circuit.

Therefore, there is a need in the art for a closed suction respiratory system that is capable of effectively cleaning the tip of a suction catheter without a resulting drop of ventilation air to the patient. Additionally, a need in the art exists in replacing a respiratory suction catheter apparatus with a new respiratory suction catheter apparatus without disconnecting the artificial airway structure from the ventilation circuit in order to prevent air loss to the patient and to lower the chance of imparting illness to the patient during the replacement procedure.

SUMMARY

Various features and advantages of the invention will be set forth in part in the following description, or may be apparent from the description, or may be learned from practice of the invention.

The present invention provides for a respiratory suction catheter apparatus that allows for a suction catheter to be removed from a ventilation circuit of a patient and replaced without having to disconnect an artificial airway structure from the ventilation circuit. The suction catheter may be adapted for removing fluid from a patient by insertion of a tubular portion into an artificial airway of the patient and application of negative pressure to a lumen of the tubular portion. A catheter attachment section may be present and has a passageway therethrough that allows for passage of the tubular portion. The catheter attachment section may have a proximal end that is attached to the suction catheter. A distal end of the catheter attachment section may be configured for releasable attachment with an artificial airway structure that is attached to the patient. Further, a valve may be located in the catheter attachment section. When closed, the valve at least substantially blocks the tubular portion of the suction catheter from the artificial airway of the patient. The valve also has an open position that allows the tubular portion of the suction catheter to be advanced through the catheter attachment section and into the artificial airway of the patient.

Also provided according to the present invention is a respiratory suction catheter apparatus that has a suction catheter with a tubular portion, lumen and distal end. The suction catheter may be adapted for removing fluids from a patient by insertion of the tubular portion into an artificial airway of the patient and application of negative pressure to the lumen. A catheter attachment section is present and has a passageway therethrough that allows for passage of the tubular portion of the suction catheter. A proximal end of the catheter attachment section may be attached to the suction catheter. A distal end of the catheter attachment section may be configured for releasable attachment with an artificial airway structure. A valve is located in the catheter attachment section and may be capable of at least substantially blocking the passageway when in a closed position. The valve has an open position that allows the tubular portion of the suction catheter to be advanced through the catheter attachment section. The catheter attachment section also has a cleaning section that is proximal from the valve when the valve is in the closed position. An irrigation port may be in communication with the cleaning section. The irrigation port may be configured for allowing fluid to be transferred therethrough into the cleaning section.

The present invention also provides for a respiratory suction catheter apparatus that has a suction catheter having a tubular portion with a lumen and distal end. The suction catheter may be adapted for removing fluids from a patient by insertion of the tubular portion into an artificial airway of the patient and application of negative pressure to the lumen. A sleeve is also present in the suction catheter and completely surrounds the tubular portion along at least a portion of the length of the tubular portion. A catheter attachment section is also provided and may have a passageway therethrough that allows for passage of the tubular portion of the suction catheter. The catheter attachment section may also have a proximal end that is attached to the suction catheter. Also, a distal end of the catheter attachment section may be configured for releasable attachment by a friction fit arrangement with an artificial airway structure that is attached to the patient. A valve is located in the catheter attachment section. The valve has a closed position in which the tubular portion of the suction catheter may be at least substantially blocked from the artificial airway of the patient. The valve has an open position that allows the tubular portion of the suction catheter to be advanced through the catheter attachment section and into the artificial airway of the patient. A cleaning section may be present and is located in the catheter attachment section proximal from the valve. Further, a wiper seal may be located in the catheter attachment section, proximal from the cleaning section.

Other exemplary embodiments of the present invention may exist in a respiratory suction catheter apparatus as described above where the valve is a single flap. In yet other exemplary embodiments, a wiper seal may be located in the catheter attachment section proximal from the valve.

In other exemplary embodiments of the present invention, the valve may be biased towards the closed position. Further, other exemplary embodiments of the present invention may include a respiratory suction catheter apparatus as described above where the single flap has an aperture therethrough. The single flap may be opened by insertion of the tubular portion through the catheter attachment section.

Other exemplary embodiments of the present invention may include a respiratory suction catheter apparatus as described above where the distal end of the catheter attachment section is releasably attachable to the artificial airway structure by a variety of mechanisms. For instance, the attachment may be effected through a friction fit arrangement, a threaded engagement, a barb structure, or a clamping ring. Additionally, the artificial airway structure onto which the respiratory suction catheter apparatus is attached may be a rotatable manifold, an elbow manifold, an elbow manifold with swiveling ports, a T-manifold, or Y-manifold in different exemplary embodiments according to the present invention.

DETAILED DESCRIPTION

Figure 1:
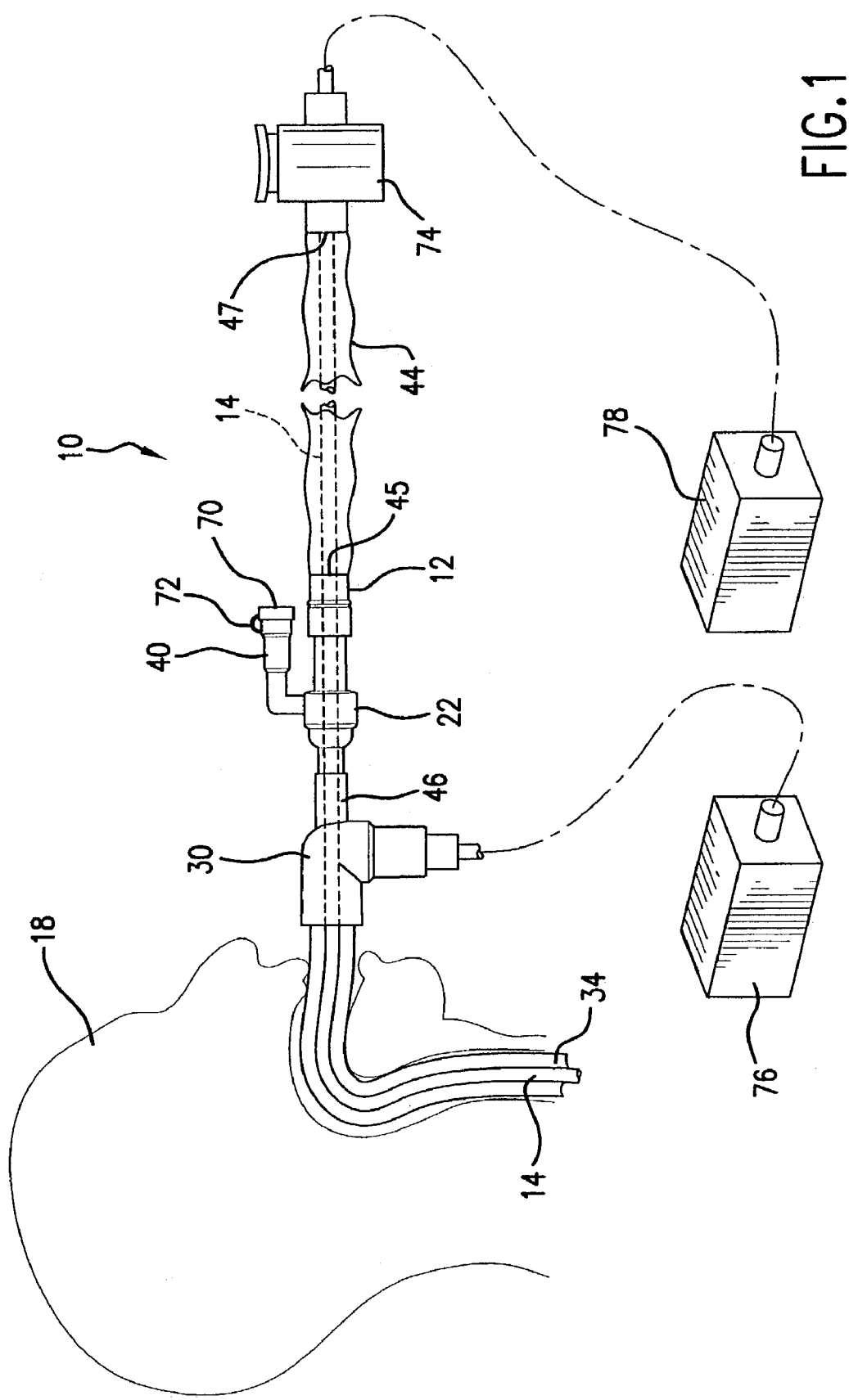
FIG. 1 is a perspective view of a respiratory suction catheter apparatus in accordance with the present invention. A patient is shown having an artificial airway and an artificial airway structure attached thereto.

Reference will now be made in detail to embodiments of the invention, one or more examples of which are illustrated in the drawings. Each example is provided by way of explanation of the invention, and is not meant as a limitation of the invention. For example, features illustrated or described as part of one embodiment can be used with another embodiment to yield still a third embodiment. It is intended that the present invention include these and other modifications and variations.

As used herein, proximal refers generally to the direction towards a medical caregiver. Also, distal refers generally to the direction towards a patient.

The present invention provides for a respiratory suction catheter apparatus 10 that allows for a suction catheter 12 to be removed from the ventilation circuit of a patient 18 and replaced without having to disconnect an artificial airway structure 30 from the ventilation circuit. Referring to the drawings, FIG. 1 shows a patient 18 having an artificial airway 34 attached thereto. A ventilator 76 may be in communication with the artificial airway 34 through an artificial airway structure 30. The artificial airway structure 30 is sometimes known in the art as a manifold. The ventilator 76 may provide air to and remove air from the patient 18 through the artificial airway 34.

If the artificial airway 34 is left in the patient 18 for any substantial amount of time, respiratory secretions may build up in the lungs of the patient 18. As such, these secretions need to be removed in order to ensure adequate lung ventilation of the patient 18 is maintained. These secretions may be removed through the use of a suction catheter 12. The suction catheter 12 has a tubular portion 14 that may be extended through the artificial airway 34 into the lungs of the patient 18. A vacuum source 78 may be in communication with the ventilation circuit, and more specifically in communication with the suction catheter 12. A medical caregiver may actuate a suction valve 74 thereby applying a vacuum pressure to the tubular portion 14. Upon doing so, respiratory secretions in the patient 18 and in the artificial airway 34 may be removed.

The respiratory suction catheter apparatus 10 is shown with a flexible plastic sleeve 44. The sleeve 44 may be present in order to contain and isolate respiratory secretions that accumulate on the tubular portion 14 of the suction catheter 12 as the tubular portion 14 is withdrawn from the ventilation circuit. The sleeve 44 may be provided on either end with sealing connections 45 and 47 that attach the sleeve 44 to the suction catheter 12.

Respiratory secretions may sometimes remain on the tubular portion 14 of the suction catheter 12 or transfer onto other portions of the ventilation circuit. These respiratory secretions are undesirable in that they provide a breeding ground for pathogens and other harmful agents that may harm the patient 18. It is therefore the case that the suction catheter 12 and/or other components of the ventilation circuit may be cleaned in order to remove any residual respiratory secretions. However, in order to ensure a lower risk of contamination to the patient 18, it may be common practice to remove and replace the suction catheter 12 and/or other components in the ventilation circuit after some amount of set time has passed, for instance after 24 or 72 hours of use.

As was previous practice, the artificial airway structure 30 was detached from the artificial airway 34 so that a new artificial airway structure 30 could be incorporated into the ventilation circuit. This break in the ventilation circuit interrupted the flow of air to the patient 18 and increased the chances of ventilator associated complications. In the present invention the respiratory suction catheter apparatus 10 may be removably attached to the artificial airway structure 30. In this instance, upon removing the respiratory suction catheter apparatus 10, the artificial airway structure 30 may remain in place and allow for communication between the ventilator 76 and the artificial airway 34. As such, air may still be provided to the patient 18 during removal of the respiratory suction catheter apparatus 10. A new respiratory suction catheter apparatus 10 may be reattached to the same artificial airway structure 30.

Figure 10:
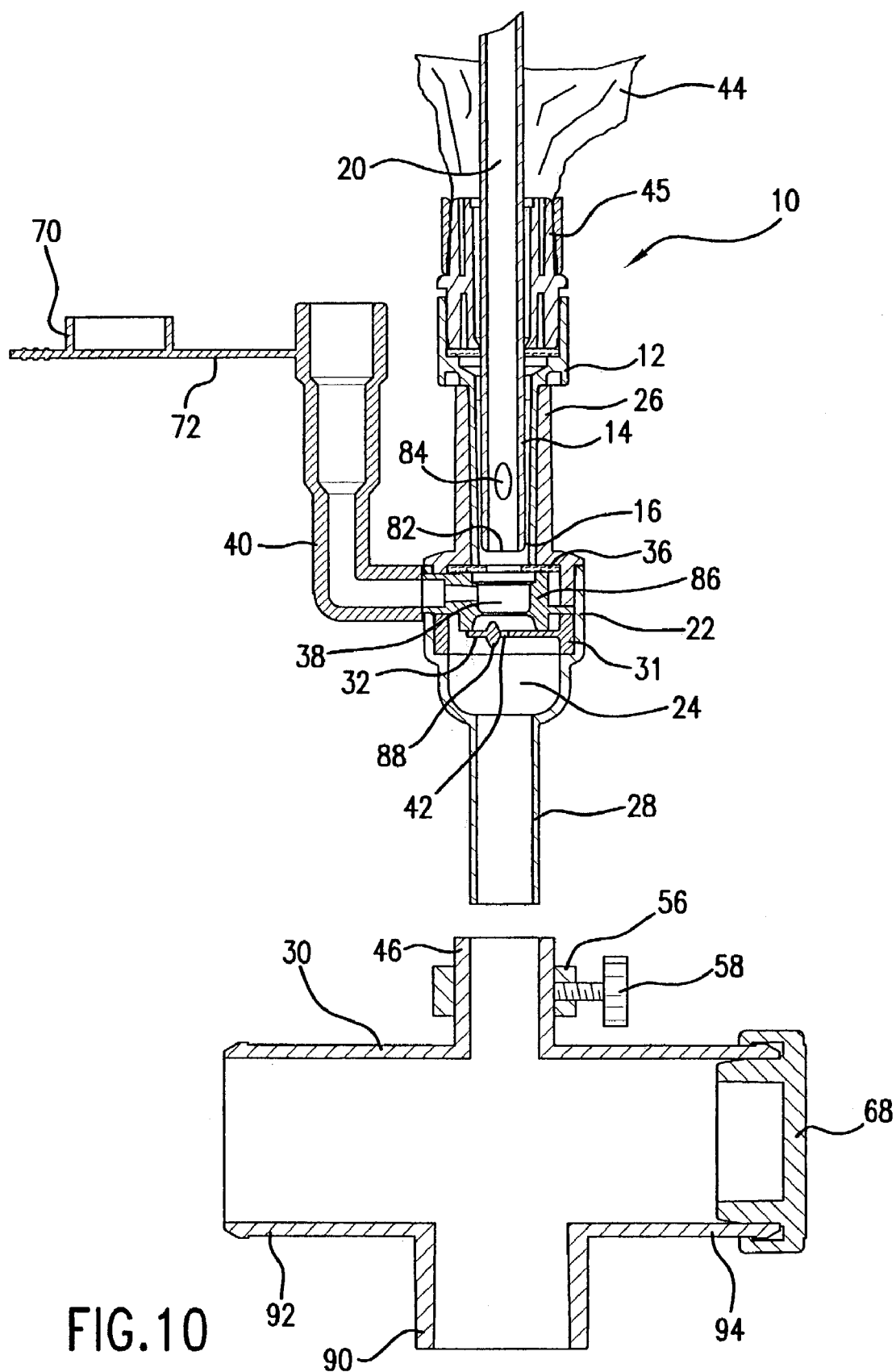
FIG. 10 is a cross sectional elevational view of a respiratory suction catheter apparatus in accordance with the present invention. Here, the respiratory suction catheter apparatus is shown as being proximate to an artificial airway structure that has a clamping ring used to attach the respiratory suction catheter apparatus to the artificial airway structure.

The respiratory suction catheter apparatus 10 in accordance with the present invention may be used in combination with a variety of artificial airway structures 30. For instance, in one exemplary embodiment of the present invention as shown in FIG. 10, the respiratory suction catheter apparatus 10 may be used with a T-piece artificial airway structure 30. A port 90 is present and may be attached to the artificial airway 34 (FIG. 1). The port 90 therefore allows for communication between the artificial airway structure 30 and the artificial airway 34. Air from the ventilator 76 (FIG. 1) may be provided to and from the artificial airway structure 30 through a port 92. The port 92 may be attached to a pair of ventilation tubes via a connector (not shown). An additional port 94 on the artificial airway structure 30 may be provided opposite the port 92. The port 94 is typically covered with a cap 68 which is removed when "blow-by" is desired to wean the patient 18 from forced ventilation. An additional port 46 may be configured to engage the respiratory suction catheter apparatus 10 such that the respiratory suction catheter apparatus 10 may be removably attached to the artificial airway structure 30.

Figure 2:
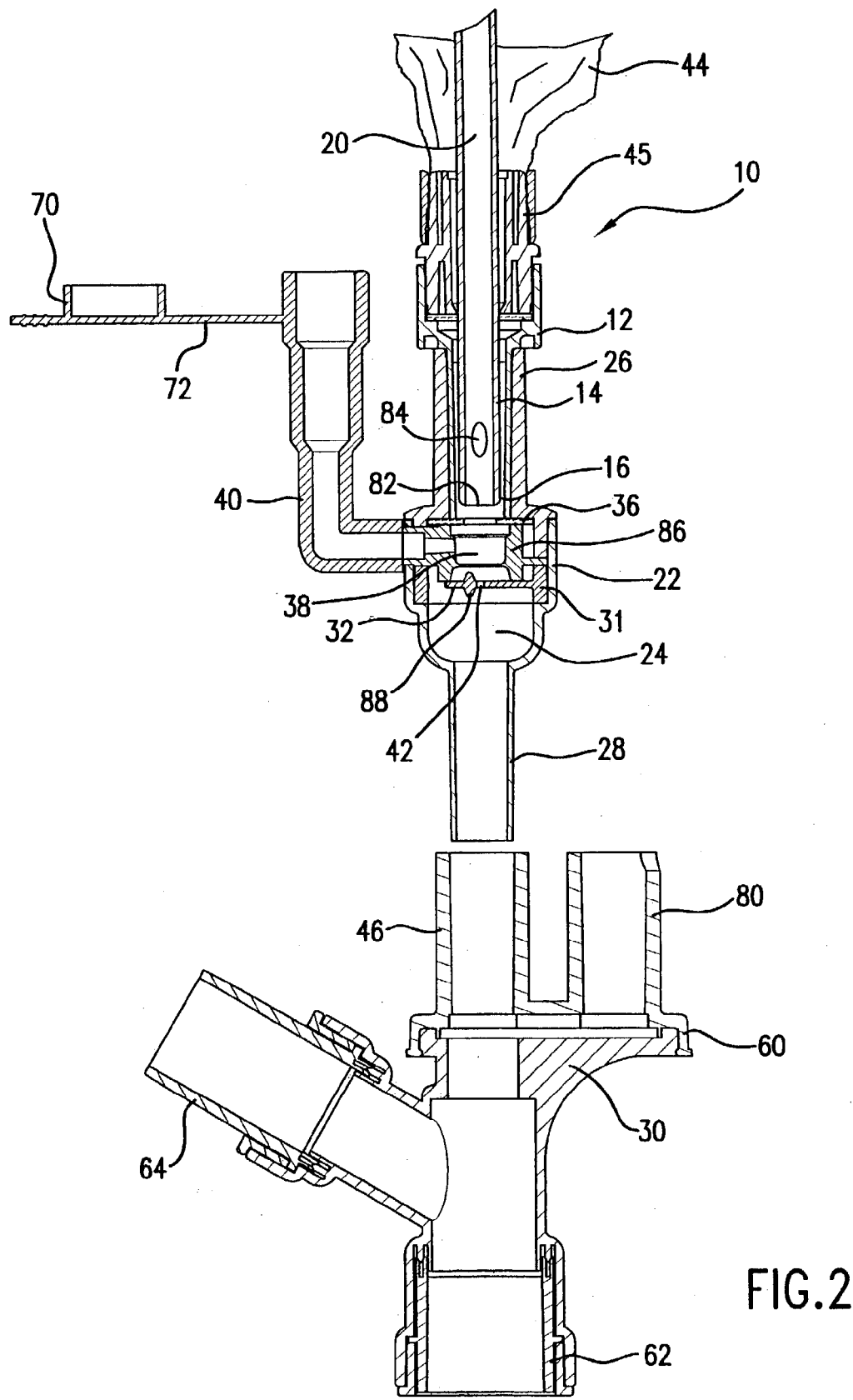
FIG. 2 is a cross sectional elevational view of a respiratory suction catheter apparatus in accordance with the present invention. The respiratory suction catheter apparatus is shown located proximate to an artificial airway structure.

The respiratory suction catheter apparatus 10 is shown in greater detail in FIG. 2. The respiratory suction catheter apparatus 10 includes a catheter attachment section 22 that may be attached to the suction catheter 12 in any suitable manner. The catheter attachment section 22 has a passageway 24 extending therethrough. The tubular portion 14 (FIG. 1) of the suction catheter 12 may be advanced through the passageway 24 and into the artificial airway structure 30, and eventually advanced into the artificial airway 34 (FIG. 1). Upon retraction of the tubular portion 14 from the patient 18, respiratory secretions may be present on the surface of the tubular portion 14. A wiper seal 36 may be provided in the catheter attachment section 22. The wiper seal 36 may be a resilient member having an aperture therethrough that allows for the tubular portion 14 to pass. The wiper seal 36 desirably tightly engages the tubular portion 14 as the tubular portion 14 is retracted from the artificial airway 34 (FIG. 1). The tubular portion 14 may be moved proximal to the wiper seal 36 and into the position shown in FIG. 2. Respiratory secretions present on the surface of the tubular portion 14 may be removed by contact with the wiper seal 36.

The catheter attachment section 22 may also be provided with a cleaning section 38. In one exemplary embodiment, the cleaning section 38 may be defined by a cleaning section member 86. Additionally or alternatively, the cleaning section 38 may be defined on one end by a valve 32. Further, the cleaning section 38 may alternatively be defined by any portion of the catheter attachment section 22. The valve 32 shown in FIG. 2 is a single flap that is hingedly attached to an annular ring 31 housed within the catheter attachment section 22. The hinge on the valve 32 may provide both a bias force and a pivoting location. Use of such a valve 32 is disclosed in U.S. Pat. No. 6,227,200 B1 issued to Crump et al., the entire disclosure of which is incorporated by reference herein in its entirety for all purposes.

The tubular portion 14 of the suction catheter 12 may have a distal end 16 with a distal opening 82. A lumen 20 may extend through the tubular portion 14 and allows for respiratory secretions and other fluids to be transferred through the distal opening 82 and into the lumen 20 by the vacuum source 78 (FIG. 1). The tubular portion 14 of the suction catheter 12 may be cleaned by positioning the distal end 16 of the suction catheter 12 either against the valve 32 and/or within the cleaning section 38. Upon so positioning, a vacuum can be effected upon the lumen 20 and lavage or other cleaning solution may be injected into the cleaning section 38. Application of the vacuum can cause the valve 32 to be forced against the distal end 16 of the tubular portion 14. In one exemplary embodiment of the present invention, the valve 32 will at least substantially block the passageway 24 when in a closed position. However, it is to be understood that injection of lavage or other cleaning solutions and/or application of a vacuum may be performed in other instances not associated with cleaning of the tubular portion 14.

Although described as contacting the distal end 16 of the suction catheter 12 in certain exemplary embodiments of the present invention the valve 32 need not contact the distal end 16 of the tubular portion 14 in order to effectively clean the tubular portion 14. For instance, the valve 32 may be urged against the cleaning section member 86 during cleaning of the tubular portion 14 of the suction catheter 12.

The tubular portion 14 may also be provided with at least one side opening 84. This arrangement allows for turbulent flow to be established within the cleaning section 38 causing the lavage solution to break up and remove any respiratory secretions present on the tubular portion 14. Respiratory secretions may be removed through the side opening 84 and/or the distal opening 82. The valve 32 may be provided with an aperture 42 therethrough. The presence of the aperture 42 may help to establish a more desirable turbulent fluid flow within the cleaning section 38. In one exemplary embodiment of the present invention, the aperture 42 is about 0.03 inches in diameter.

An irrigation port 40 may be attached to the catheter attachment section 22 in order to allow for the injection of the lavage solution. A container (not shown) holding the lavage solution may have an outlet inserted into the irrigation port 40. Lavage may then be dispensed from this container into the irrigation port 40 which may be in communication with the cleaning section 38. The irrigation port 40 may also be provided with an irrigation cap 70 that may be connected to the irrigation port 40 by way of a tether 72. The irrigation cap 70 may be placed onto the irrigation port 40 in order to close the irrigation port 40 when not in use.

In certain exemplary embodiments of the present invention, the cleaning section member 86 may be configured such that a small amount of space is present between the tubular portion 14 of the suction catheter 12 and the cleaning section member 86. In certain exemplary embodiments of the present invention, this space may be between about 0.005 and about 0.015 inches. This space provides two advantages. First, if lavage is needed to be provided to the patient 18, injection of lavage through the irrigation port 40 and then into the cleaning section 38 causes a stream of lavage solution to be directed out of the catheter attachment section 22 and into the patient 18. Second, as the tubular portion 14 is withdrawn the close proximity between the tubular portion 14 and the cleaning section member 86 may help to wipe any heavy layers of respiratory secretions from the outside of the tubular portion 14 of the suction catheter 12.

Employment of the valve 32 is advantageous in that the tubular portion 14 of the suction catheter 12 may be cleaned without causing a pressure loss to the ventilation circuit. This is because the valve 32 substantially isolates the portion of the respiratory suction catheter apparatus 10 proximal the valve 32 from the remainder of the ventilation circuit. In one exemplary embodiment of the present invention, the valve 32 may be provided with one or more projections 88.

Figure 9:
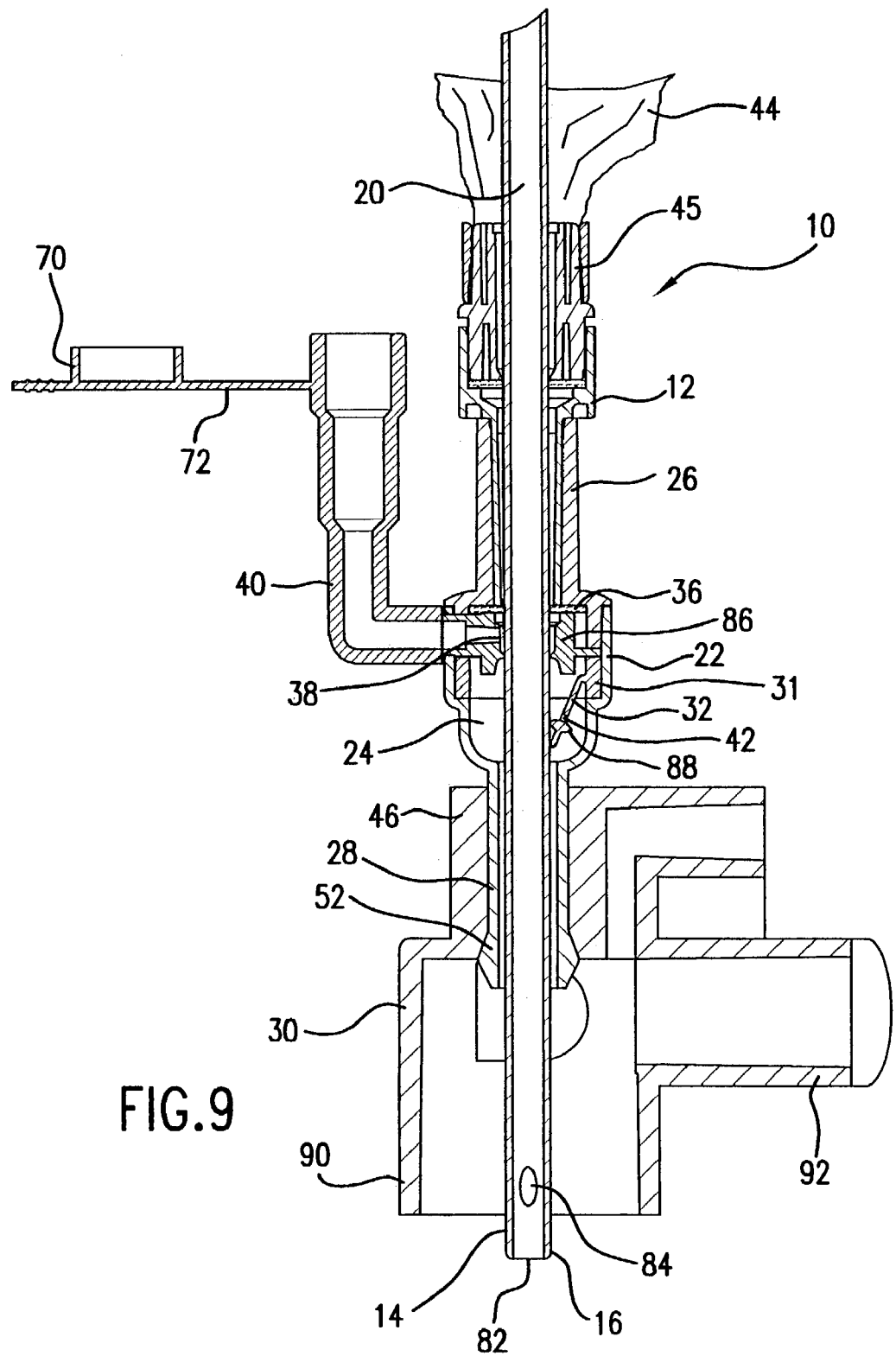
FIG. 9 is a cross sectional elevational view of a respiratory suction catheter apparatus similar to that shown in FIG. 8. Here, the respiratory suction catheter apparatus is shown engaging the artificial airway structure, and a tubular portion of a suction catheter is shown passing through the respiratory suction catheter apparatus and the artificial airway structure.

FIG. 9 shows the respiratory suction catheter apparatus 10 engaged with the artificial airway structure 30. In this case, the artificial airway structure 30 may be a neonate manifold. The tubular portion 14 of the suction catheter 12 is shown advanced through the catheter attachment section 22, the artificial airway structure 30, and out of the port 90 eventually enabling entry into the artificial airway 34 (FIG. 1) of the patient 18 (FIG. 1). The valve 32 may be opened by insertion of the tubular portion 14 through the catheter attachment section 22. The projection 88 may be configured to minimize valve 32 contact with the surface of the tubular portion 14. This contact helps to reduce contamination of respiratory secretions from the tubular portion 14 onto the valve 32 and related components due to the minimized contact afforded by the projections 88. Additionally, in certain exemplary embodiments this contact may help to ensure the structural integrity of the valve 32 and may minimize any unnecessary bending or stress on the valve 32.

In one exemplary embodiment of the present invention, the valve 32 is biased towards the closed position. Although shown in FIG. 9 as being attached to an annular ring 31, the valve 32 may alternatively be attached, for example, directly onto a wall of the catheter attachment section 22. The valve 32 may be configured to be closed once the tubular portion 14 is positioned proximally from the valve 32, or alternatively the valve 32 may be configured to be closed upon the proximal positioning of the tubular portion 14 from the valve 32 and application of vacuum through the lumen 20 in order to draw the valve 32 into a closed position.

In other exemplary embodiments of the present invention the valve 32 need not be a single flap, nor need the flap be attached to the annular ring 31, nor need it have the aperture 42, or the projection 88. It is to be understood that the configuration of the valve 32 shown in the drawings is only a desired embodiment, and other configurations of the valve 32 are possible in accordance with the present invention. For instance, the valve 32 may be one, two, or three flaps that are biased towards a closed position and opened by insertion of the tubular portion 14 of the suction catheter 12 through the catheter attachment section 22.

Figure 3:
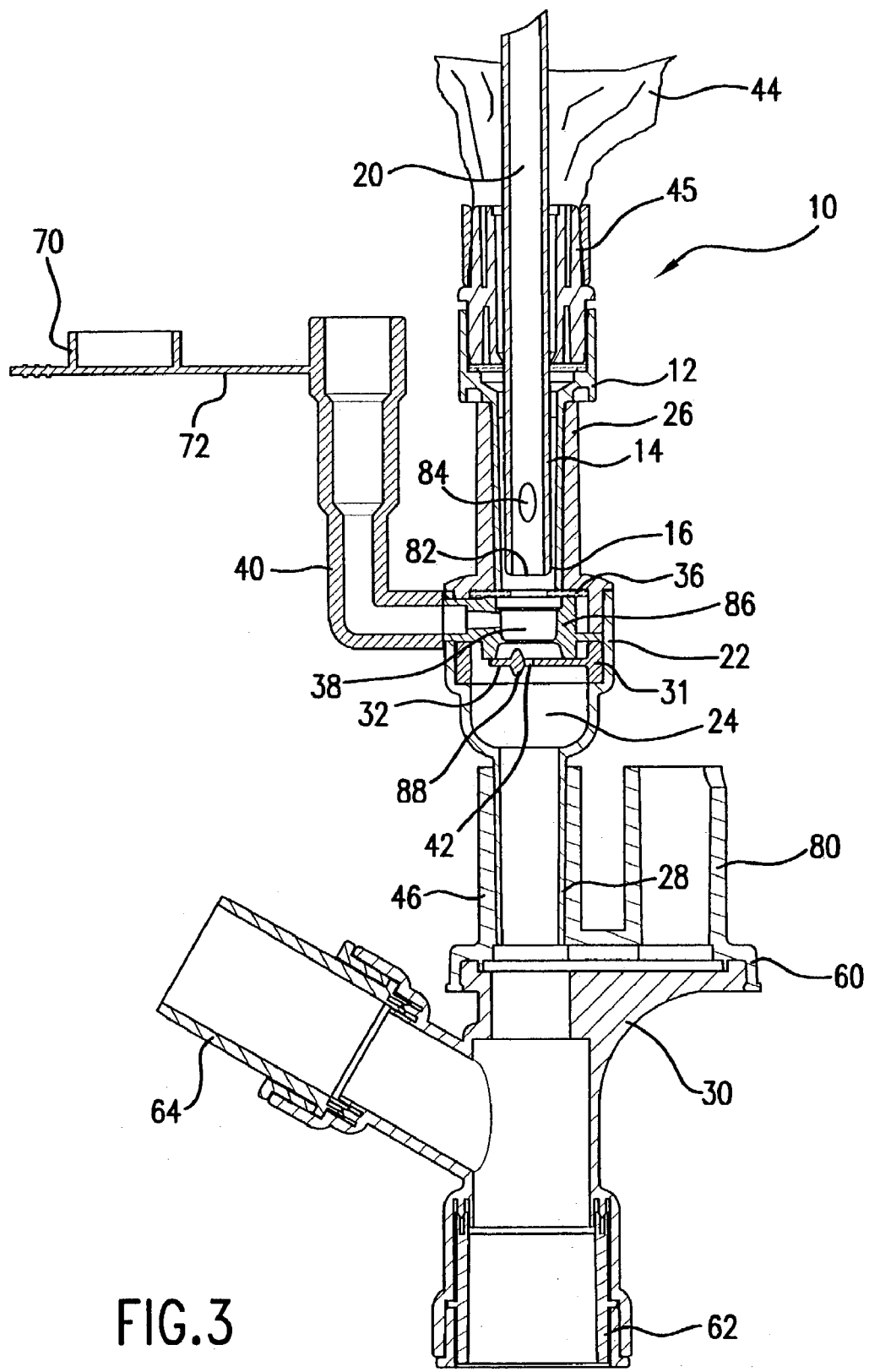
FIG. 3 is a cross sectional elevational view of a respiratory suction catheter apparatus similar to that shown in FIG. 2. Here, the respiratory suction catheter apparatus is attached to the artificial airway structure.

Referring back to FIG. 2, the catheter attachment section 22 is provided with a proximal end 26 and a distal end 28. The proximal end 26 may be permanently attached to the suction catheter 12 through a variety of means commonly known in the art. For instance, these two components may be force fit to one another, integrally molded with one another, or sonically welded to one another. The distal end 28 of the catheter attachment section 22 is configured for being releasably attachable to a port 46 on the artificial airway structure 30. Engagement of the distal end 28 of the catheter attachment section 22 and the port 46 is shown in FIG. 3. In this exemplary embodiment, the distal end 28 is friction fit onto the port 46. This provides for a secure attachment between the respiratory suction catheter apparatus 10 and the artificial airway structure 30, but also allows for the disengagement of these two components once the need to replace the respiratory suction catheter apparatus 10 is present. The artificial airway structure 30 shown in FIG. 3 may be provided with an additional port 80 onto which the respiratory suction catheter apparatus 10 may be attached in other exemplary embodiments. Additionally, in yet other exemplary embodiments of the present invention two respiratory suction catheter apparatuses 10 may be employed such that their respective distal ends 28 of their respective catheter attachment section 22 are engageable with the port 46 and the port 80. It should be appreciated that other medical instruments besides an additional respiratory suction catheter apparatus 10 may be alternatively engaged with the port 80.

As shown in FIG. 3, the port 46 is in axial alignment with a swiveling port 62 that may be further attached to the artificial airway 34. A rotating member 60 may be provided on the artificial airway structure 30 that allows for the rotation of the ports 46 and 80 such that port 80 may be axially aligned with the swiveling port 62, hence moving port 46 out of axial alignment with the port 62. This type of artificial airway structure 30 is disclosed in U.S. Pat. No. 5,735,271 to Lorenzen et al., the entire disclosure of which is incorporated by reference herein in its entirety for all purposes. The artificial airway structure 30 has another swiveling port 64 located thereon that is in communication with the ventilator 76 (FIG. 1). These two ports 62 and 64 may be provided with a swiveling feature so that the tubing and/or structure connected to them more easily moves when various parts of the ventilation circuit are manipulated or moved. This helps to reduce stress imparted onto the patient 18 (FIG. 1) brought about by movement of the ventilation circuit. The swiveling ports 62 and 64 may be constructed, for instance, as those disclosed in U.S. Pat. No. 5,694,922 to Palmer, the entire disclosure of which is incorporated by reference herein in its entirety for all purposes.

Figure 4:
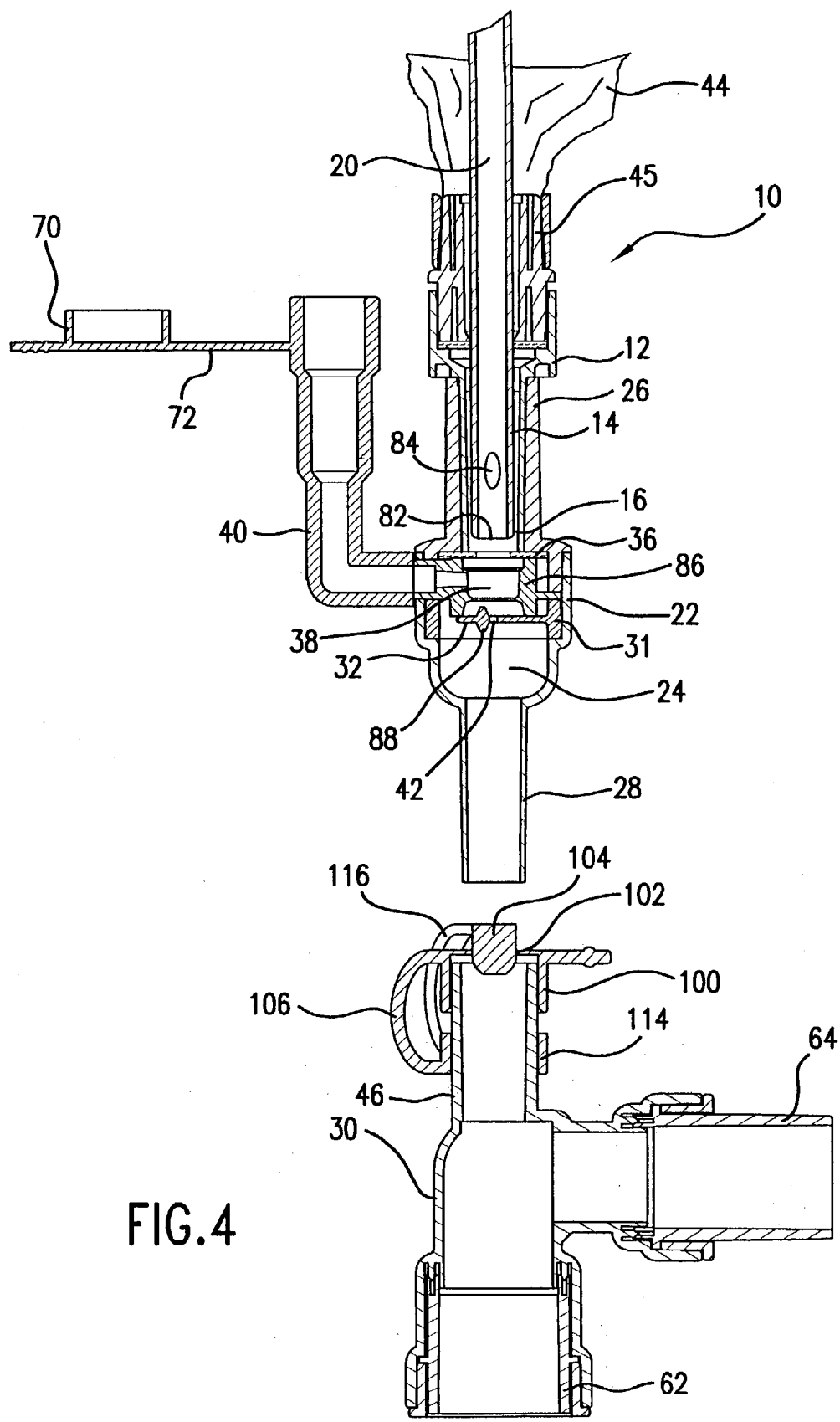
FIG. 4 is a cross sectional elevational view of a respiratory suction catheter apparatus in accordance with the present invention. Here, the respiratory suction catheter apparatus is located proximate to an artificial airway structure that has swiveling ports.
Figure 5:
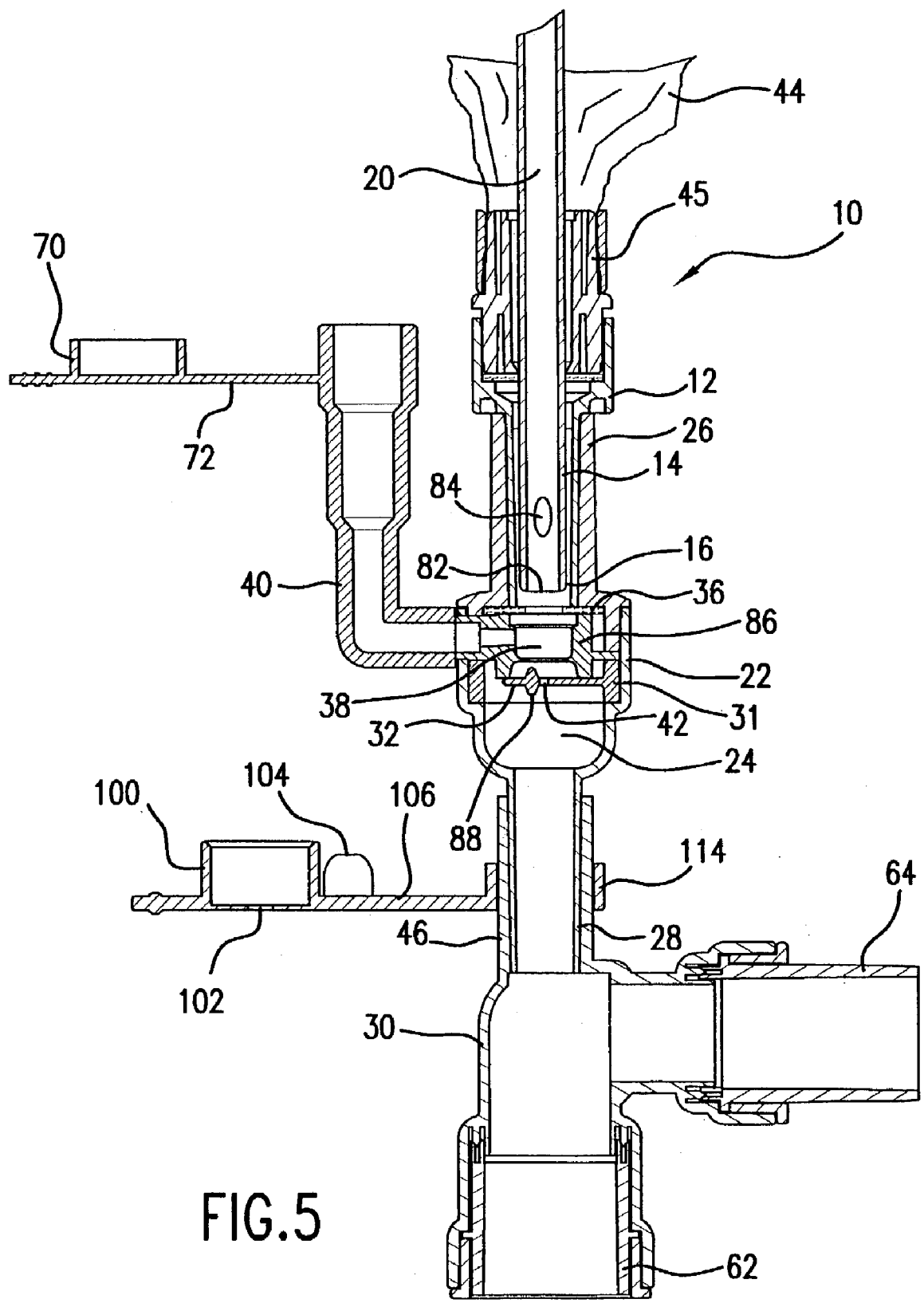
FIG. 5 is a cross sectional elevational view of a respiratory suction catheter apparatus similar to that shown in FIG. 4. Here, the respiratory suction catheter apparatus is attached to the artificial airway structure through a friction fit arrangement.

Another exemplary embodiment of the present invention is shown in FIG. 4. Here, the respiratory suction catheter apparatus 10 may be substantially similar to the respiratory suction catheter apparatus 10 described above with respect to the exemplary embodiment shown in FIG. 2. However, the artificial airway structure 30 to which the respiratory suction catheter apparatus 10 may be removably attached is in this instance an elbow manifold that has a pair of swiveling ports 62 and 64. FIG. 5 shows the respiratory suction catheter apparatus 10 attached to the artificial airway structure 30 in much the same way as discussed above with respect to the exemplary embodiment shown in FIG. 3, that being a friction fit arrangement between the port 46 and the distal end 28 of the catheter attachment section 22. It is to be understood that the present invention is not limited to a particular amount of friction between the port 46 and the distal end 28 of the catheter attachment section 22. For instance these two parts may be tightly fit with respect to one another such that a medical caregiver must provide a large amount of force in order to remove the distal end 28 of the catheter attachment section 22 from the port 46. Conversely, these two parts may be fit together such that only a small amount of force is needed to remove the distal end 28 of the catheter attachment section 22 from the port 46. The present invention is to be understood as encompassing exemplary embodiments of the respiratory suction catheter apparatus 10 that may be fit onto the artificial airway structure 30 with varying degrees of friction between these two components.

Although shown (in FIGS. 3, 5, 7, 9, 11, and 13) as inserted within the port 46, the distal end 28 of the catheter attachment section 22 may in other exemplary embodiments be sized to fit around the port 46. Additionally, other friction fit arrangements between the port 46 and the distal end 28 of the catheter attachment section 22 are possible in accordance with the present invention as is commonly known in the art. Other suitable connections such as a snap fit, a latch, a boss and detent, etc. may be used.

Figure 6:
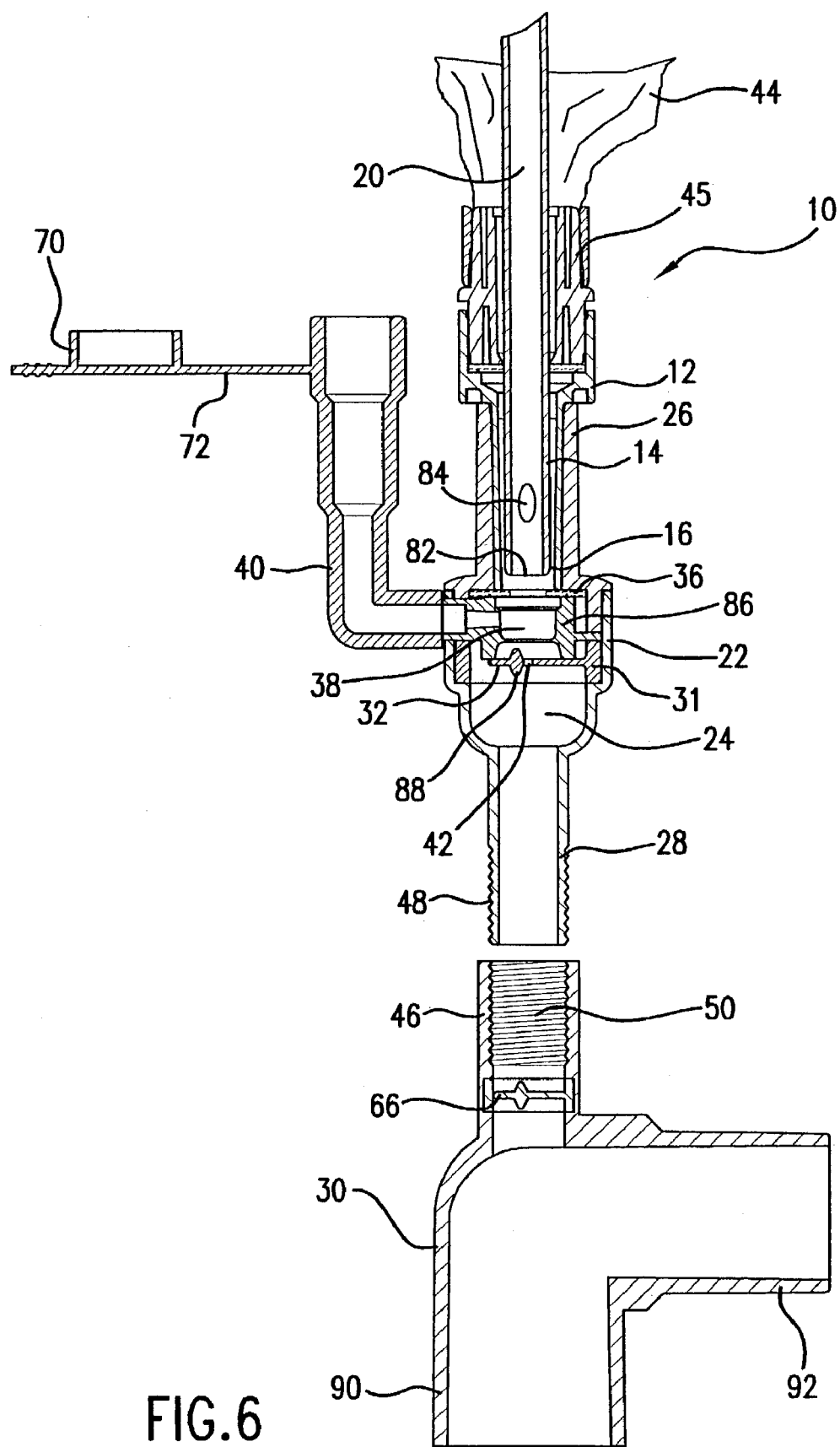
FIG. 6 is a cross sectional elevational view of a respiratory suction catheter apparatus in accordance with the present invention. The respiratory suction catheter apparatus is shown located proximate to an artificial airway structure that has an artificial airway structure valve located therein.

Yet another exemplary embodiment of the present invention is disclosed in FIG. 6. Here, the artificial airway structure 30 may be an elbow manifold that has ports 90 and 92 located thereon that do not include the swiveling feature. These two ports 90 and 92 form part of the ventilation circuit that provides air to and from the patient 18 (FIG. 1) through the port 90 and provides air to and from the ventilator 76 (FIG. 1) through the port 92. As stated, the respiratory suction catheter apparatus 10 may be disengaged from the artificial airway structure 30 without the need to remove the artificial airway structure 30 from the remainder of the ventilation circuit. This helps to ensure that air is still provided to the patient 18 (FIG. 1) during replacement of the respiratory suction catheter apparatus 10. However, it may be the case that a small amount of air is lost due to the opening in the port 46 once the respiratory suction catheter apparatus 10 is disengaged therefrom. In order to further minimize the loss of positive end expiratory pressure, the artificial airway structure 30 may be provided with an artificial airway structure valve 66.

The artificial airway structure valve 66 may prevent air loss during removal of the respiratory suction catheter apparatus 10 by sealing off the port 46. The artificial airway structure valve 66 may take any design commonly known in the art. For instance, as disclosed in FIG. 6, the artificial airway structure valve 66 may be a single flap that is substantially similar to the valve 32 of the catheter attachment section 22. The artificial airway structure valve 66 may be biased towards a closed position, and may be opened upon insertion of the tubular portion 14 (FIG. 1) through the port 46 and into the port 90. Although shown as a single flap, the artificial airway structure valve 66 may also be a plurality of flaps.

Additionally, the artificial airway structure valve 66 may be a mechanism that does not have flaps but yet still provides for a closed port 46 during disengagement of the respiratory suction catheter apparatus 10 from the artificial airway structure 30.

Additionally, the valve 32 and the artificial airway structure valve 66 may be of other configurations in other exemplary embodiments of the present invention. For instance, configurations disclosed in commonly owned U.S. Pat. No. 6,227,200 B1 issued to Crump et al., may be employed which may be a twisting membrane, a duckbill arrangement, or a dual membrane configuration having offset apertures.

The artificial airway structure valve 66 may be configured such that it is closed during disengagement of the respiratory suction catheter apparatus 10, but opened upon insertion of the distal end 28 of the catheter attachment section 22 into the port 46. Additionally, the artificial airway structure valve 66 may be configured to be opened by insertion of the tubular portion 14 of the suction catheter 12 through the port 46 and into the artificial airway structure 30. In this instance, it may be the case that the artificial airway structure valve 66 is also in need of cleaning due to contact with respiratory secretions from the tubular portion 14. In this instance, the distal end 16 of the tubular portion 14 may be located proximate to the artificial airway structure valve 66, and lavage solution may be injected into this location through the irrigation port 40. Vacuum may be applied to the lumen 20 of the tubular portion 14 and respiratory secretions present may then be removed via a process substantially the same as the cleaning procedure with respect to the valve 32.

Figure 7:
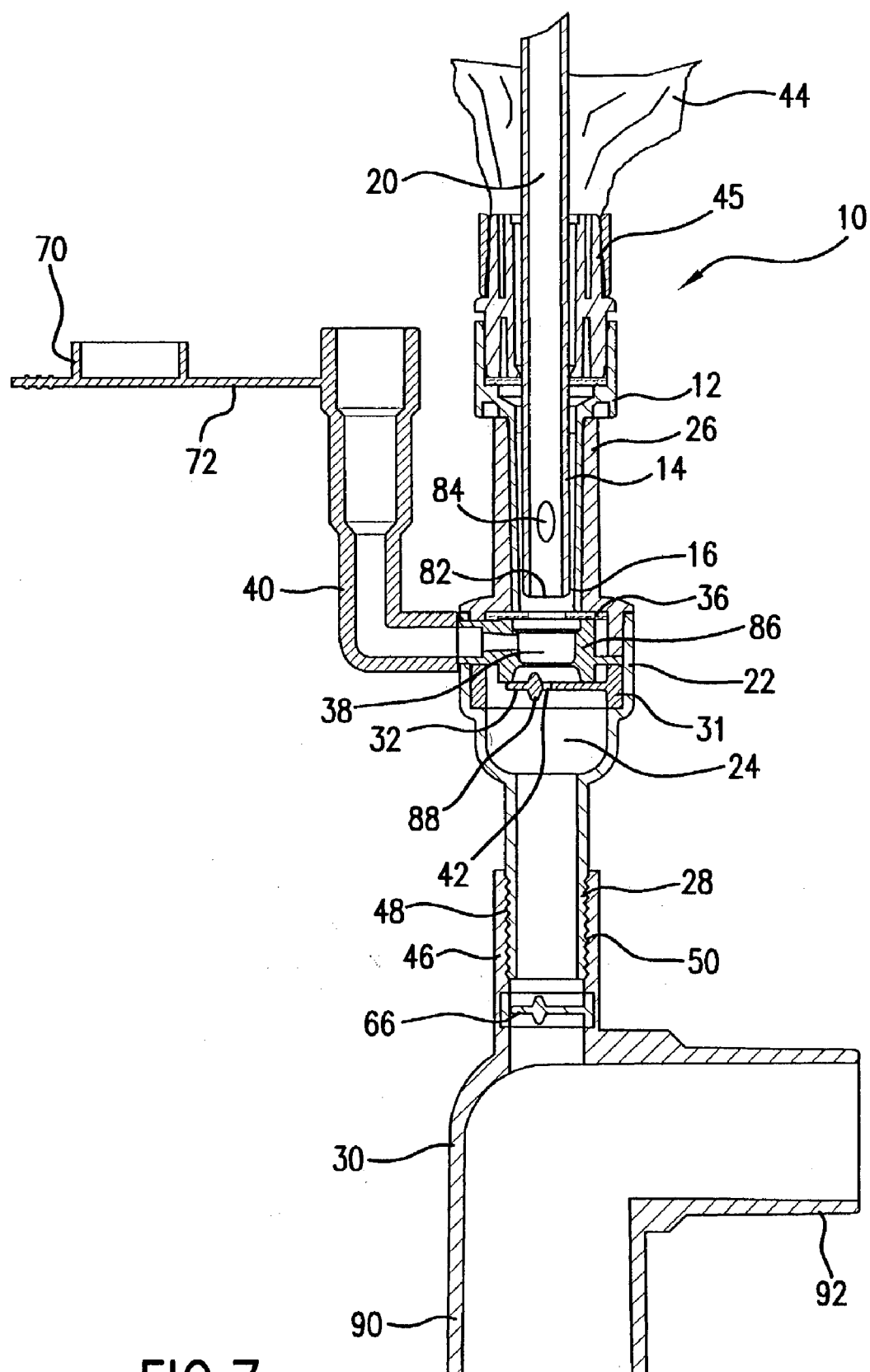
FIG. 7 is a cross sectional elevational view of a respiratory suction catheter apparatus similar to that shown in FIG. 6. Here, the respiratory suction catheter apparatus is connected to the artificial airway structure through a threaded engagement.

Additionally, other ways of releasably attaching the respiratory suction catheter apparatus 10 to the artificial airway structure 30 are possible in accordance with the present invention. FIG. 6 shows a threaded engagement where the distal end 28 has external threading 48 located thereon. The port 46 has internal threading 50 located therein and is configured to mate with the external threading 48. FIG. 7 shows the threaded engagement between the respiratory suction catheter apparatus 10 and the artificial airway structure 30. In order to effect this attachment, the medical caregiver needs to rotate the respiratory suction catheter apparatus 10 and the artificial airway structure 30 with respect to one another. Although shown as an internal connection between the outside of the distal end 28 of the catheter attachment section 22 and the inside of the port 46 in FIGS. 3, 5, 7, 9, 11, and 13, it is to be understood that in other exemplary embodiments, attachment of the distal end 28 of the catheter attachment section 22 to the exterior of the port 46 is possible.

Figure 8:
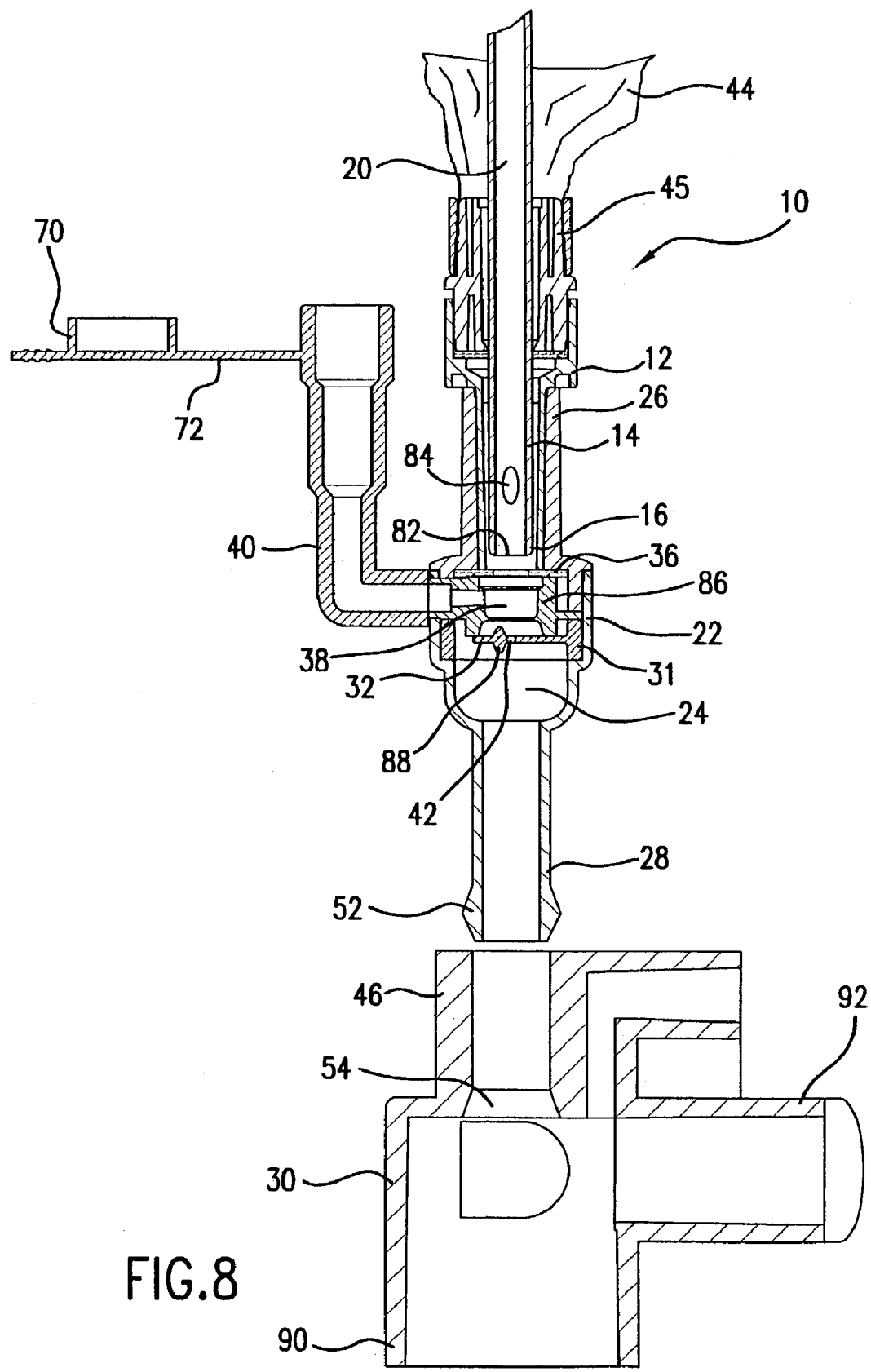
FIG. 8 is a cross sectional elevational view of a respiratory suction catheter apparatus in accordance with the present invention. A barb is present on the respiratory suction catheter apparatus which is used to connect the respiratory suction catheter apparatus to an artificial airway structure.

Another way of releasably attaching the respiratory suction catheter apparatus 10 to the artificial airway structure 30 is disclosed in FIG. 8. Here, the artificial airway structure 30 is a neonate manifold having a plurality of ports. Three such ports are labeled 46, 90, and 92. The port 92 provides access to and from the ventilator 76 (FIG. 1), and the port 90 provides access to and from the artificial airway 34 (FIG. 1) of the patient 18 (FIG. 1). The port 46 is configured to be releasably engageable with the distal end 28 of the respiratory suction catheter apparatus 10. The distal end 28 of the catheter attachment section 22 is provided with a barb 52. The barb 52 and the distal end 28 may be force fit into the port 46 and slid distally. The port 46 is provided on one end with a receiving area 54 that is designed to receive the barb 52. As the barb 52 is moved into the receiving area 54, the distal end 28 of the catheter attachment section 22 is retained in the port 46. This engagement is shown in FIG. 9. In order to remove the respiratory suction catheter apparatus 10 from the artificial airway structure 30, the medical caregiver may provide a force tending to separate these two components. This force will be enough to compress the barb 52 and/or deform the distal end 28 such that they may be slid out of the port 46 and effect disengagement of the respiratory suction catheter apparatus 10.

Figure 11:
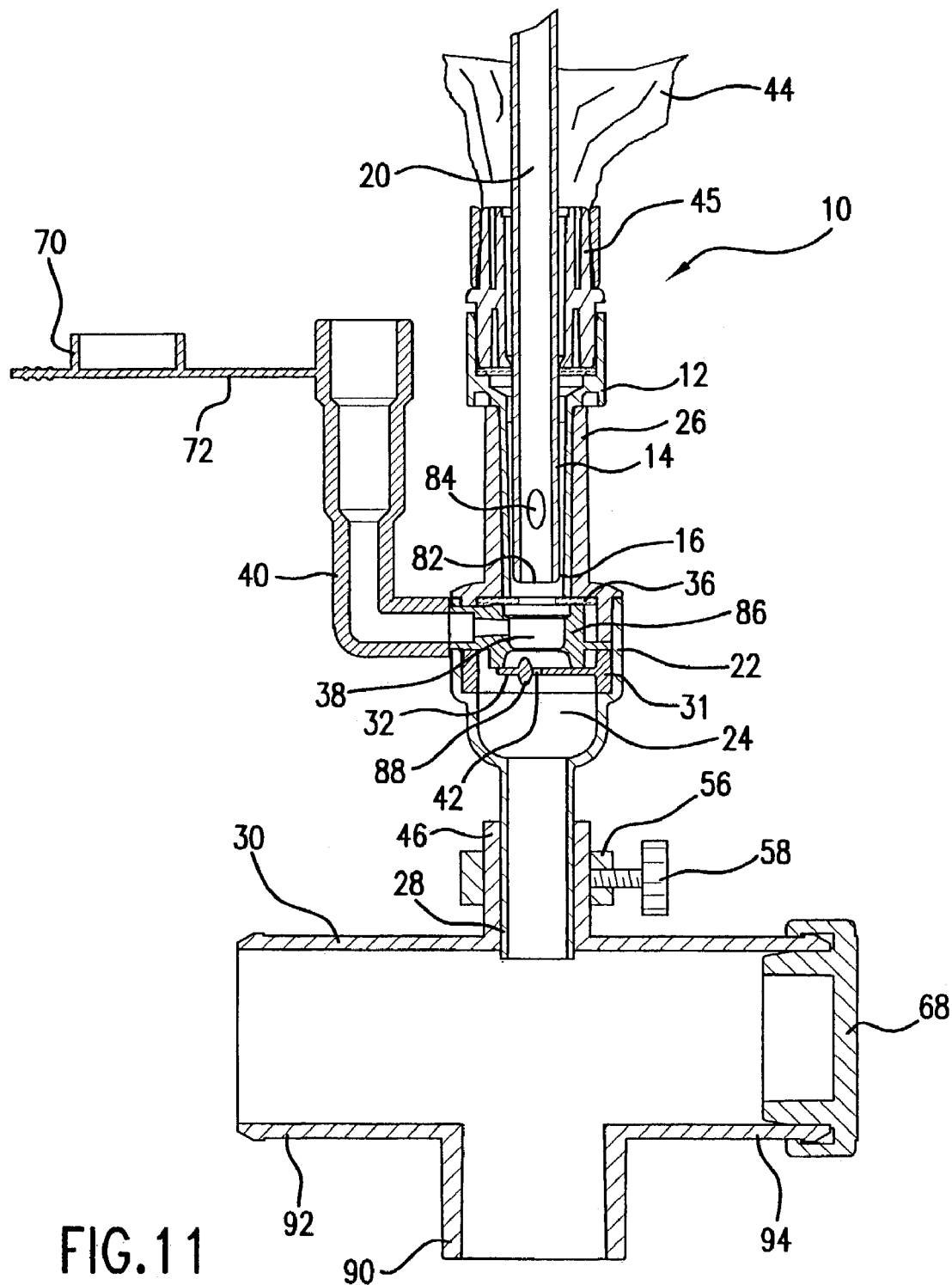
FIG. 11 is a cross sectional elevational view of a respiratory suction catheter apparatus similar to that shown in FIG. 10. Here, the respiratory suction catheter apparatus is attached to the artificial airway structure.

Yet another exemplary embodiment of the present invention is shown in FIG. 10. Here, the artificial airway structure 30 may be a T-piece manifold, having the port 46 located thereon in order to be releasably attached to the distal end 28 of the respiratory suction catheter apparatus 10. A clamping ring 56 may be provided and surrounds the exterior of the port 46. The clamping ring 56 may be a single piece of material, for instance metal or medical grade plastic, that exhibits at least a slight amount of flexibility. The clamping ring 56 has holes (not shown) on either end through which a screw 58 may be positioned. The distal end 28 of the catheter attachment section 22 may be inserted into the port 46 as shown in FIG. 11, and the screw 58 may be turned such that the two ends of the clamping ring 56 are urged towards one another. This in turn causes the port 46 to be compressed such that it is forced against the distal end 28 of the catheter attachment section 22 causing a secure attachment between the respiratory suction catheter apparatus 10 and the artificial airway structure 30. Additionally, a nut (not shown) may engage the screw 58 and may also be used to effect the constriction of the clamping ring 56 as is commonly known in the art. The screw 58 may be loosened in order to separate the two ends of the clamping ring 56 from one another. This loosens the connection between the distal end 28 and the port 46 and allows for the respiratory suction catheter apparatus 10 to be removed from the artificial airway structure 30.

Figure 12:
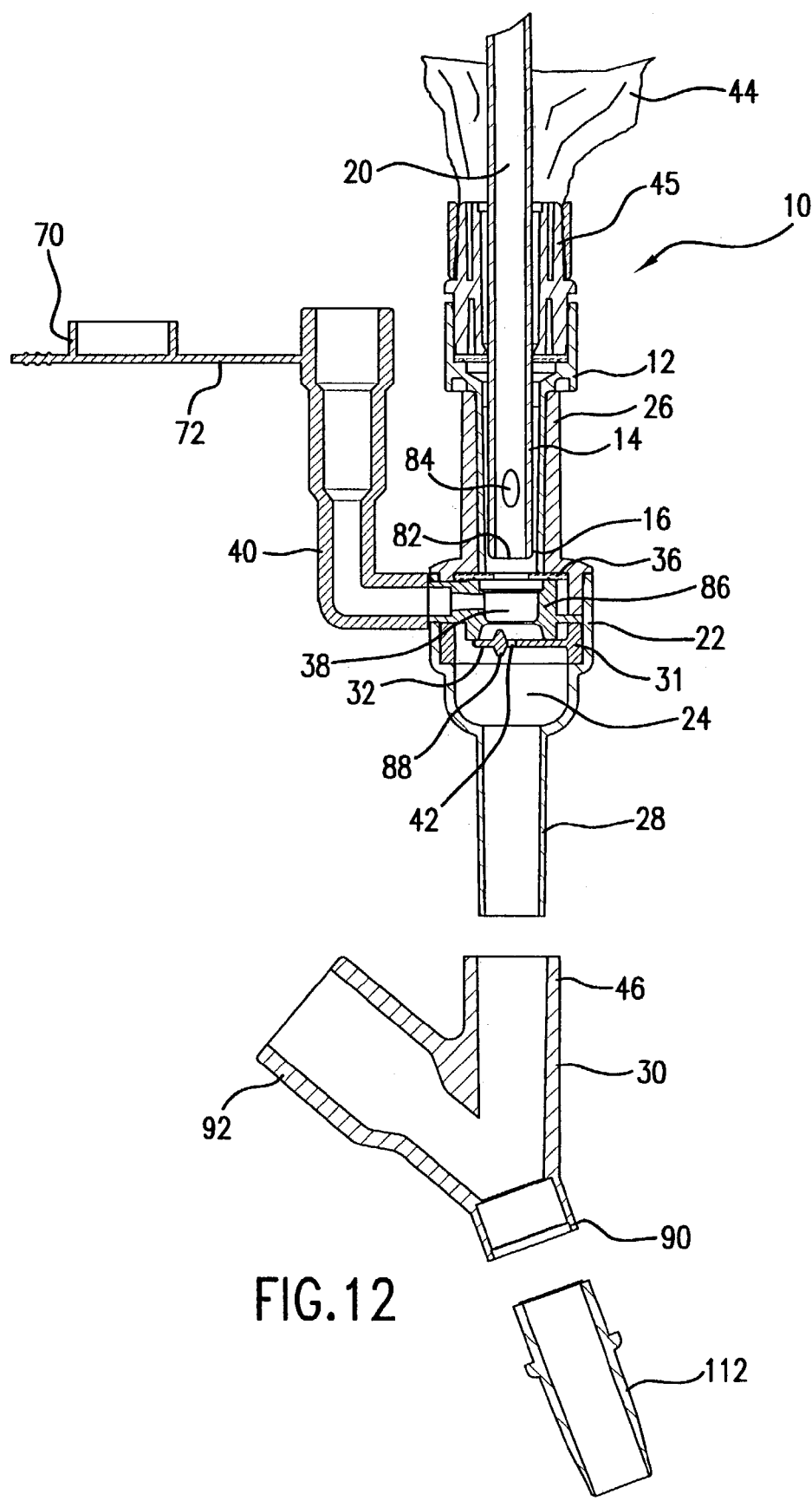
FIG. 12 is a cross sectional elevational view of a respiratory suction catheter apparatus in accordance with the present invention. Here, the respiratory suction catheter apparatus is located proximate to an artificial airway structure that is a Y-manifold.
Figure 13:
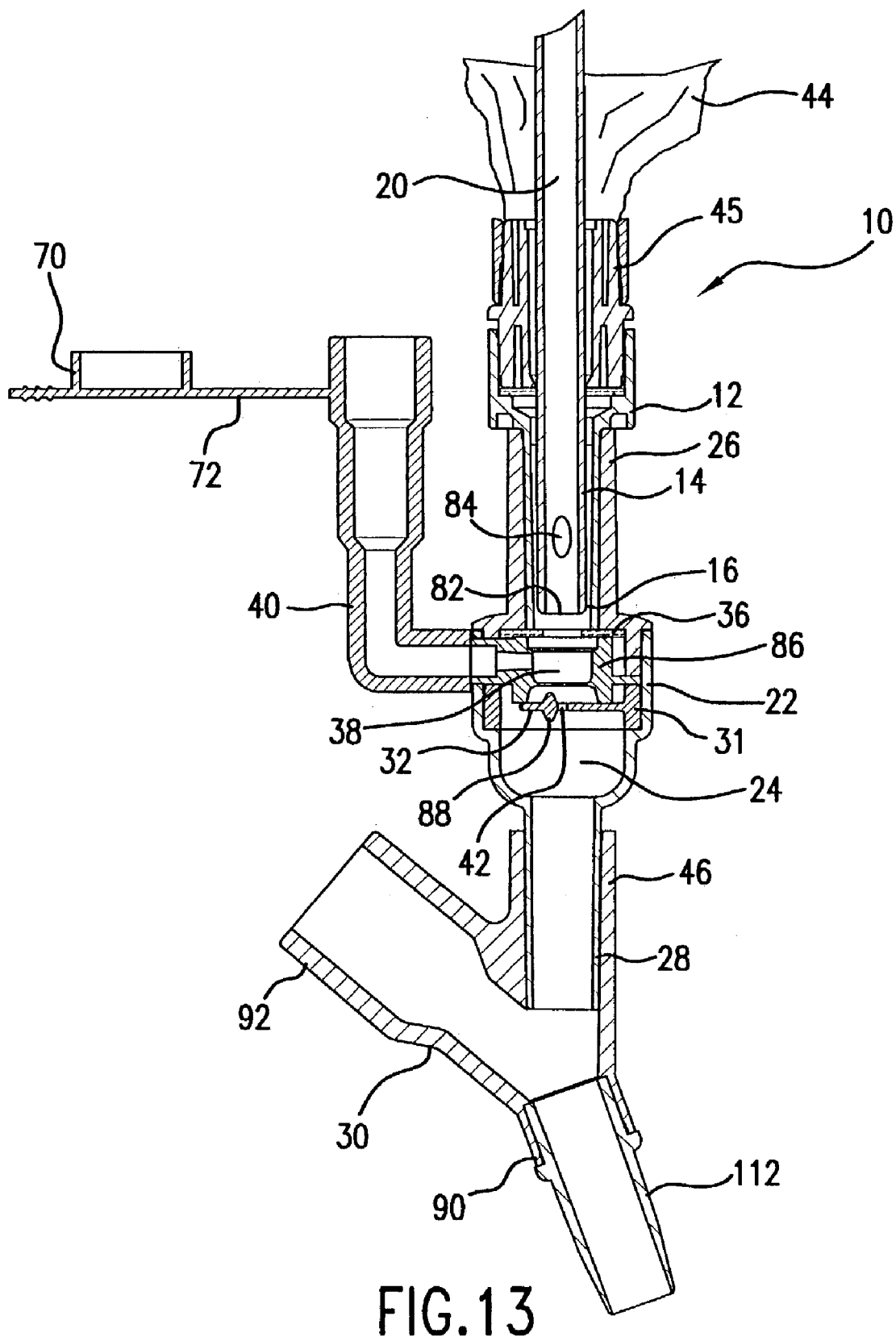
FIG. 13 is a cross sectional elevational view of a respiratory suction catheter apparatus similar to that shown in FIG. 12. Here, the respiratory suction catheter apparatus is connected to the artificial airway structure through a fiction fit arrangement.

An additional exemplary embodiment of the present invention is shown in FIG. 12. Here, the respiratory suction catheter apparatus 10 is configured substantially the same as the respiratory suction catheter apparatus 10 of FIG. 2. However, the artificial airway structure 30 onto which it is releasably attached is shown as a neonate Y-manifold. FIG. 13 shows the distal end 28 of the catheter attachment section 22 connected to the port 46 on the artificial airway structure 30 through a friction fit arrangement as previously described. Ports 90 and 92 of the artificial airway structure 30 allow for communication between the ventilator 76 (FIG. 1) and the artificial airway 34 (FIG. 1). A tapered adaptor 112 may be retained within the port 90 in order to allow for connection of the respiratory suction catheter apparatus 10 to tubing or other components of the ventilation circuit. The tapered adaptor 112 may or may not be permanently attached to the port 90. Alternatively, the artificial airway structure 30 itself may be tapered, hence eliminating the need for the tapered adaptor 112 in other exemplary embodiments of the present invention.

In accordance with the present invention, the respiratory suction catheter apparatus 10 may be sized such that it may be attached to a variety of artificial airway structures 30. As such, the present invention includes various sizes of the respiratory suction catheter apparatus 10 along with various sizes and configurations of the artificial airway structure 30. The examples of which described herein are only exemplary embodiments of the present invention and do not limit the present invention. Additionally, various ways of releasably attaching the distal end 28 to the artificial airway structure 30 are possible in accordance with the present invention, the mechanisms disclosed herein are only exemplary embodiments.

Figure 14:
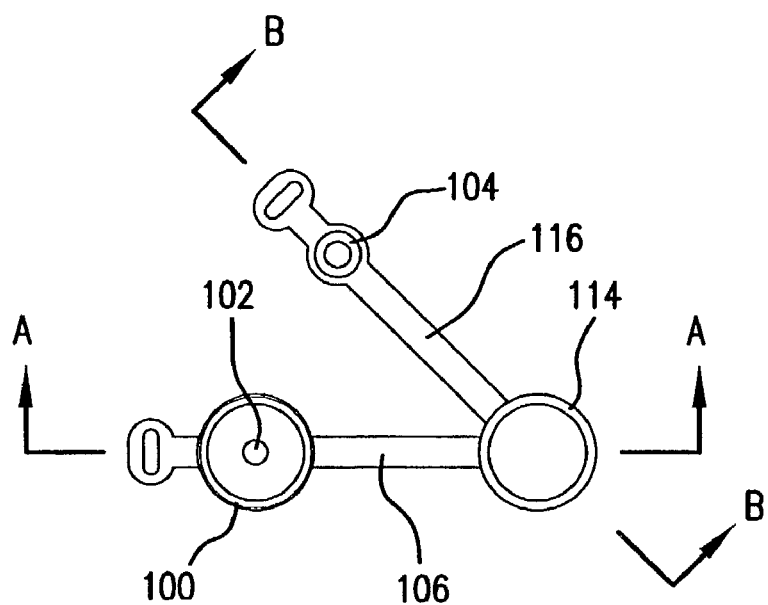
FIG. 14 is a top plan view of a cap and plug assembly in accordance with one exemplary embodiment of the present invention.
Figure 15:
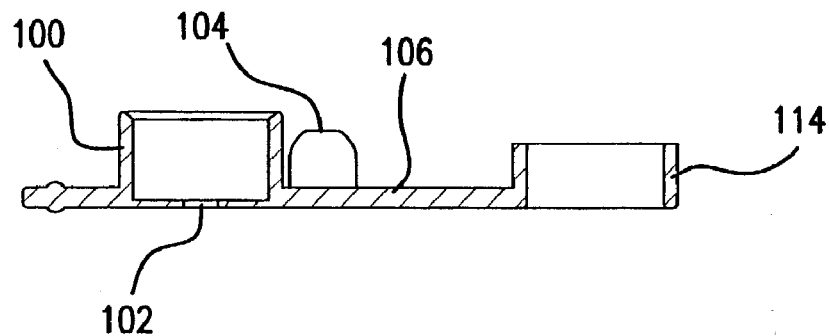
FIG. 15 is a cross sectional view taken along line A—A in FIG. 14.
Figure 16:
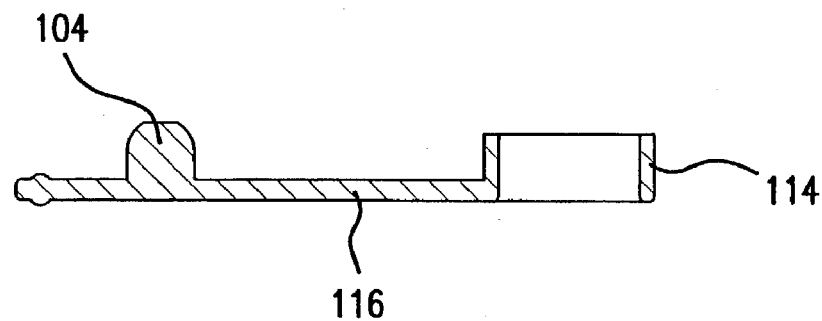
FIG. 16 is a cross sectional view taken along line B—B in FIG. 14.

The respiratory suction catheter apparatus 10 may be provided with a cap 100 as shown in FIGS. 14–16. An attachment member 114 is connected to the cap 100 by way of a tether 106. Additionally, a plug 104 is also connected to the attachment member 114 by way of a plug tether 116. The cap 100 is provided with an opening 102.

The cap 100 may be attached to the artificial airway structure 30 as shown in FIG. 4. Here, the cap 100 is placed over the port 46, and the plug 104 is inserted into the opening 102. As such, the artificial airway structure 30 may be isolated from the environment and will be able to maintain positive and expiratory pressure during detachment of the respiratory suction catheter apparatus 10. The cap 100 may be attached to the artificial airway structure 30 by the attachment member 114 that is connected to any portion of the artificial airway structure 30. FIG. 4 shows the attachment member 114 connected to the port 46. FIG. 5 shows the cap 100 and the plug 104 removed from the port 46, and the insertion of the distal end 28 of the catheter attachment section 22 into the port 46 and the artificial airway structure 30. However, it is to be understood that in other exemplary embodiments of the present invention, the plug 104 may be removed, but the cap 100 may be still retained on the port 46. In this instance, the distal end 28 is fit through the opening 102 and engages the port 46 through a friction fit arrangement with the cap 100 still present on the port 46.

It should be understood that the present invention includes various modifications that can be made to the embodiments of the respiratory suction catheter apparatus described herein as come within the scope of the appended claims and their equivalents.

What is claimed:

1. A respiratory suction catheter apparatus, comprising:
   a suction catheter having a tubular portion with a distal end and a lumen, the suction catheter adapted for removing fluids from a patient by insertion of the tubular portion into an artificial airway of the patient and the application of negative pressure to the lumen;
   a catheter attachment section comprising:
      a passageway therethrough allowing for passage of the tubular portion of the suction catheter;
      a proximal end attached to the suction catheter; and
      a distal end configured for releasable attachment within an artificial airway structure attached to the patient such that the distal end of the catheter attachment section is concentric within the artificial airway structure; and
   a valve located entirely within the distal end of the catheter attachment section so as not to contact the artificial airway structure and to be removed with the catheter attachment section, the valve having a closed position in which the tubular portion of the suction catheter is at least substantially blocked from the artificial airway of the patient, the valve having an open position allowing the tubular portion of the suction catheter to be advanced through the catheter attachment section and into the artificial airway of the patient.

2. The respiratory suction catheter apparatus of claim 1, further comprising a wiper seal located entirely within the distal end of the catheter attachment section proximal from the valve.

3. The respiratory suction catheter apparatus of claim 1, further comprising:
   a cleaning section located in the catheter attachment section proximal from the valve; and
   an irrigation port in communication with the cleaning section, the irrigation port configured for allowing fluid to be transferred therethrough into the cleaning section.

4. The respiratory suction catheter apparatus of claim 1, wherein the valve is a single flap.

5. The respiratory suction catheter apparatus of claim 4, wherein the single flap has an aperture therethrough, the single flap is adapted to be opened by insertion of the tubular portion through the catheter attachment section.

6. The respiratory suction catheter apparatus of claim 1, wherein the suction catheter has a sleeve that completely surrounds the tubular portion along at least a portion of the length of the tubular portion.

7. The respiratory suction catheter apparatus of claim 1, wherein the valve is biased towards the closed position.

8. The respiratory suction catheter apparatus of claim 1, wherein the distal end of the catheter attachment section is adapted to be releasably attachable to the artificial airway structure by a friction fit arrangement.

9. The respiratory suction catheter apparatus of claim 1, wherein the distal end of the catheter attachment section has threading thereon for being releasably attachable to the artificial airway structure by a threaded engagement.

10. The respiratory suction catheter apparatus of claim 1, wherein the distal end of the catheter attachment section has at least one barb located thereon for being releasably attachable to the artificial airway structure.

11. The respiratory suction catheter apparatus of claim 1, further comprising a clamping ring engageable with the distal end of the catheter attachment section and adapted to releasably attach the catheter attachment section to the artificial airway structure.

12. The respiratory suction catheter apparatus of claim 1, wherein the artificial airway structure is selected from the group consisting of a rotatable manifold, an elbow manifold, a T-manifold, and a Y-manifold.

13. The respiratory suction catheter apparatus of claim 1, wherein the artificial airway structure has a valve located therein for preventing air loss.

14. The respiratory suction catheter apparatus of claim 1, further comprising:
   a cap configured to engage a port of the artificial airway structure, the cap having an opening that allows for insertion of the tubular portion into the artificial airway structure; and
   a plug having a plug tether, the plug insertable into the opening in the cap.

15. A respiratory suction catheter apparatus, comprising:
   a suction catheter having a tubular portion with a distal end and a lumen, the suction catheter adapted for removing fluids from a patient by insertion of the tubular portion into an artificial airway of the patient and the application of negative pressure to the lumen;
   a catheter attachment section comprising:
      a passageway therethrough allowing for passage of the tubular portion of the suction catheter;
      a proximal end attached to the suction catheter;
      a distal end configured for releasable attachment within an artificial airway structure such that the distal end of the catheter attachment section is concentric within the artificial airway structure;
      a valve located entirely within the catheter attachment section so as not to contact the artificial airway structure and to be removed with the catheter attachment section, the valve capable of at least substantially blocking the passageway when in a closed position and having an open position allowing the tubular portion of the suction catheter to be advanced through the catheter attachment section; and
      a cleaning section within the distal end of catheter attachment section proximal from the valve when the valve is in the closed position; and
   an irrigation port in communication with the cleaning section, the irrigation port configured for allowing fluid to be transferred therethrough into the cleaning section.

16. The respiratory suction catheter apparatus of claim 15, further comprising a wiper seal located in the catheter attachment section proximal from the valve.

17. The respiratory suction catheter apparatus of claim 15, wherein the valve is a single flap.

18. The respiratory suction catheter apparatus of claim 15, wherein the valve is a single flap and has an aperture therethrough, the single flap is adapted to be opened by insertion of the tubular portion through the catheter attachment section.

19. The respiratory suction catheter apparatus of claim 15, wherein the suction catheter has a sleeve that completely surrounds the tubular portion along at least a portion of the length of the tubular portion.

20. The respiratory suction catheter apparatus of claim 15, wherein the valve is biased towards the closed position.

21. The respiratory suction catheter apparatus of claim 15, wherein the distal end of the catheter attachment section is releasably attachable to the artificial airway structure by a friction fit arrangement.

22. The respiratory suction catheter apparatus of claim 15, wherein the distal end of the catheter attachment section has threading thereon for being releasably attachable to the artificial airway structure by a threaded engagement.

23. The respiratory suction catheter apparatus of claim 15, wherein the distal end of the catheter attachment section has at least one barb located thereon for being releasably attachable to the artificial airway structure.

24. The respiratory suction catheter apparatus of claim 15, further comprising a clamping ring engageable with the distal end of the catheter attachment section and adapted to releasably attach the catheter attachment section to the artificial airway structure.

25. The respiratory suction catheter apparatus of claim 15, wherein the artificial airway structure is selected from the group consisting of a rotatable manifold, an elbow manifold, a T-manifold, and a Y-manifold.

26. The respiratory suction catheter apparatus of claim 15, wherein the artificial airway structure has a valve located therein for preventing air loss.

27. A respiratory suction catheter apparatus, comprising:
   a suction catheter having a tubular portion with a distal end and a lumen, the suction catheter adapted for removing fluids from a patient by insertion of the tubular portion into an artificial airway of the patient and the application of negative pressure to the lumen, the suction catheter having a sleeve that completely surrounds the tubular portion along at least a portion of the length of the tubular portion;
   a catheter attachment section comprising:
      a passageway therethrough allowing for passage of the tubular portion of the suction catheter;
      a proximal end attached to the suction catheter; and
      a distal end configured for releasable attachment by a friction fit arrangement within an artificial airway structure attached to the patient;
   a valve located completely within the catheter attachment section so as not to contact the artificial airway structure, the valve having a closed position in which the tubular portion of the suction catheter is at least substantially blocked from the artificial airway of the patient, the valve having an open position allowing the tubular portion of the suction catheter to be advanced through the catheter attachment section and into the artificial airway of the patient;
   a cleaning section located in the catheter attachment section proximal from the valve; and
   a wiper seal located in the catheter attachment section proximal from the cleaning section.

* * * * *